US00PP08334P

United States Patent [19]

Bull

[11] Patent Number: Plant 8,334

[45] Date of Patent: Aug. 3, 1993

[54] IMPATIENS PLANT NAMED ANNA

[76] Inventor: Norbert Bull, Gärtnersiedlung 2, 2351 Gönnebek, Fed. Rep. of Germany

[21] Appl. No.: 802,856

[22] Filed: Dec. 6, 1991

[51] Int. Cl.[5] ..... A01H 5/00
[52] U.S. Cl. ..... Plt./87.6
[58] Field of Search ..... Plt./87.6

*Primary Examiner*—James R. Feyrer
*Attorney, Agent, or Firm*—Foley & Lardner

[57] ABSTRACT

An impatiens plant named Anna, characterized by its large, intense cherry-red flower color, early flowering, floriferous habit, compact growth habit, medium size green foliage, and its adaptability to pot plant, patio, or bedding plant culture.

2 Drawing Sheets

1

The present invention relates to a new and distinctive cultivar of impatiens plant, botanically known as Impatiens, and referred to be the cultivar name Anna. The new cultivar was developed by me through controlled breeding by crossing seed or female parent identified as seedling No. 1 with male or pollen parent identified as Seedling No. 2. Both parents are unreleased and propriety lines.

Asexual reproduction of the new cultivar by the inventor by terminal or stem cuttings taken at Gönnebek, Federal Republic of Germany has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Unique bright cherry red flower color.
2. Compact growth habit.
3. Medium size, green foliage.
4. Very floriferous habit, and early flowering.
5. Suitable for pot plant, patio or bedding plant culture.

Anna is difficult to compare with existing cultivars due to its flower color, which is a new and distinct bright cherry red.

The accompanying colored photographs illustrate the overall appearance of this cultivar, showing the colors as true as it is reasonably possible to obtain in a colored reproduction of this type.

The photo at the top of sheet 1 comprises a top perspective view of a potted plant of Anna.

The bottom photo on sheet 1 shows a single flower (top side), and top and bottom views of a typical leaf.

The photograph on sheet 2 shows the upper side and under side of typical flowers, a bud with attached spur, and the upper side and bottom side of typical leaves. Scales in centimeters are included to show the size of these parts.

The following is a detailed description of my new impatiens cultivar based on plants produced under normal commercial practice at Gönnebek, Federal Republic of Germany.

Color references are made to the Royal Horticultural Society (RHS) Colour Chart except where general terms of ordinary dictionary significance are used.

Parentage: Controlled cross between Bull Unnamed Seedling No. 1 × Bull Unnamed Seedling No. 2.

2

Propagation:

*Type cutting.*—Stem 15–22 mm long will grow to 4–5 cm in 20 days.

*Time to initiate roots.*—8 days at 22° C. summer. 10 days at 20° C. winter.

*Rooting habit.*—Rapid rooting.

Plant description:

*Form.*—Symmetrically mounded, self-branching.

*Habit of growth.*—Compact growth habit. Eight (8) weeks after sticking stem cuttings in 12 cm pots, plant is approximately 32 cm in diameter and 32 cm in height, measured from top of pot.

*Foliage description.*—(1) Size: Medium in length and width. Length is approximately 9 cm and width 4 cm at point of maximum width. (2) Shape: Generally ovate, with acute to acuminate tip and rounded to acute base; see photos. (3) Margin: Mildly serrated. (4) Color: (a) Young foliage upper surface: Green, slightly darker than RHS 147A. (b) Under surface: Light greyed-green. (c) Mature foliage upper surface: Green, slightly darker than RHS 147A. (d) Under surface: Light greyed-green approximately 191A. (5) Veination: Light red midvein on upper side and darker red veins on under side (see photo). (6) Variegation: None.

Flowering description:

*Flowering habit.*—Flowers from leaf whorl in uniform manner.

*Natural flowering season.*—March until October.

*Flower buds.*—Typical; cherry-red in color.

*Flowers borne.*—On pedicels; red-purple in color.

*Quantity of flowers.*—Very floriferous, many flowers per plant. Flowers both mask the crown and occur above the leaf canopy.

*Spur.*—Downwardly curved from base of calyx, approximately 4–5 cm in length and red-purple in color.

*Longevity.*—Flowers are long lasting and non-fading.

*Petals.*—Number of petals: Five (5). Shape: Generally heart-shaped but slightly elongated (see photo). Color: Upper surface: 45B; top photo makes it appear that the flower is bicolored but this is due to light reflection; color is solid. Under surface: Same as for top side, only slightly lighter. Size of flower: Large, approximately 6 cm. in diameter.

Reproductive organs:

*Stamens.*—Five (5).

*Anthers.*—Hooded, cherry-red in color.

*Pollen color.*—Pale yellow.

*Stigma.*—Five in number, pale yellow in color.

*Styles.*—Yellow in color.

*Ovary.*—5 in number, size 3–5 mm., green-brown in color.

Disease resistance: No disease problems noted to date.

I claim:

1. A new and distinct impatiens plant named Anna, as illustrated and described.

* * * * *

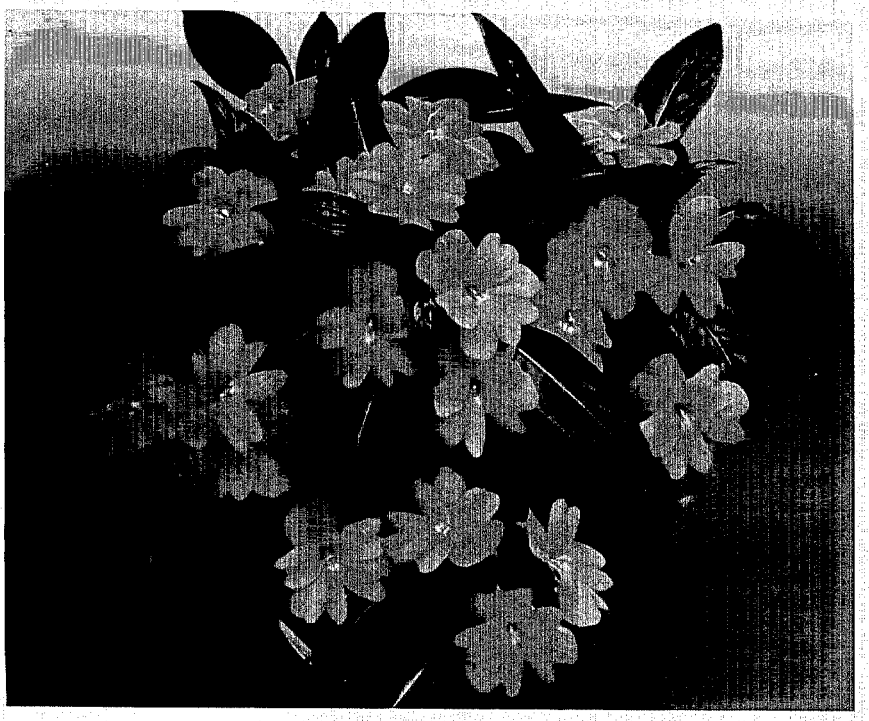
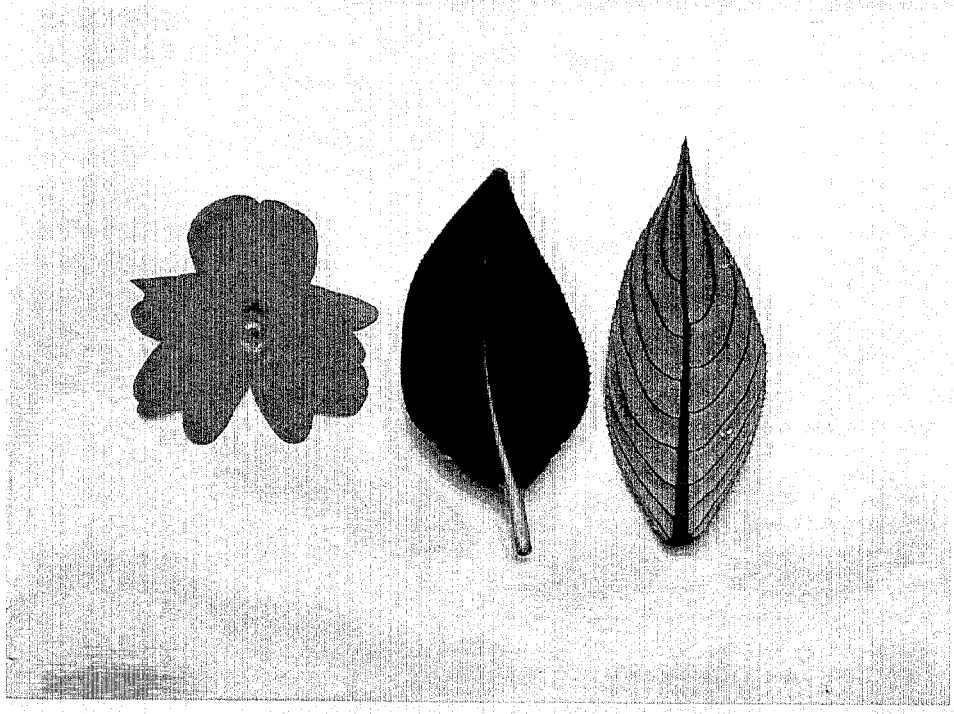

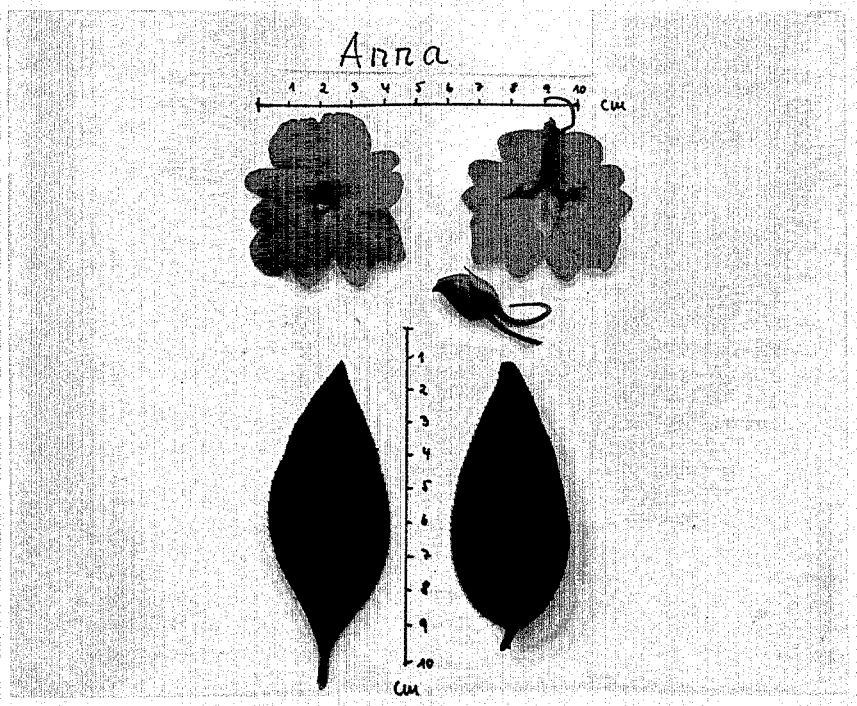
Anna
1 2 3 4 5 6 7 8 9 10
CM
1
2
3
4
5
6
7
8
9
10
CM